(12) United States Patent
Cerundolo et al.

(10) Patent No.: US 6,689,742 B1
(45) Date of Patent: Feb. 10, 2004

(54) NY-ESO-1 PEPTIDE DERIVATIVES, AND USES THEREOF

(75) Inventors: Vincenzo Cerundolo, Heddington (GB); Rodney Dunbar, Heddington (GB); Ji-li Chen, Heddington (GB)

(73) Assignee: Chancellors, Masters and Scholars of the University of Oxford, Oxford (GB)

( * ) Notice: Subject to any disclaimer, the term of this patent is extended or adjusted under 35 U.S.C. 154(b) by 0 days.

(21) Appl. No.: 09/514,036

(22) Filed: Feb. 25, 2000

(51) Int. Cl.$^7$ ............................ A61K 38/04; C07K 7/00
(52) U.S. Cl. ........................ 514/2; 514/15; 530/328
(58) Field of Search ..................... 530/328; 514/15, 514/2

(56) References Cited

FOREIGN PATENT DOCUMENTS

| WO | WO 98/14464 | * | 4/1998 |
|----|-------------|---|--------|
| WO | WO 99/18206 | * | 4/1999 |

OTHER PUBLICATIONS

Rammensee et al. Immunogenetics 41: 178–228, 1995.*
Drijfthout et al. Human Immunol. 43: 1–12, 1993.*
Valmori, et al., "Naturally Occurring Human Lymphocyte Antigen–A2 Restricted CD8$^{8+}$ T–Cell Response to the Cancer Testis Antigen NY–ESO–1 in Melanoma Patents," Canc. Res. 60:4499–4506 (Aug. 15, 2000).
Chen, et al., "Identification of NY–ESO–1 Peptide Analogues Capable of Improved Stimulation of Tumor Reactive CTL," J. Immunol 165: 948–955 (2000).
Rimoldi, et al., "Efficient Stimultaneous Presentation of NY–ESO–1/LAGE–1 Primary and Nonprimary Open Reading Frame Derived CTL Epitopes in Melanoma," J. Immunol 165: 7253–7261 (2000).

* cited by examiner

*Primary Examiner*—Christina Chan
*Assistant Examiner*—Marianne DiBrino
(74) *Attorney, Agent, or Firm*—Fulbright & Jaworski LLP

(57) ABSTRACT

The invention relates to variant peptides which bind to HLA molecules, leading to lysis of cells via cytolytic T cell lines. The variants are based upon NY-ESO-1 peptides. The peptides can be incorporated into immune tetramers, which are useful as T cell sorters.

14 Claims, No Drawings

SEQUENCE LISTING

```
<160> NUMBER OF SEQ ID NOS: 18

<210> SEQ ID NO 1
<211> LENGTH: 11
<212> TYPE: PRT
<213> ORGANISM: Homo sapiens

<400> SEQUENCE: 1

Ser Leu Leu Met Trp Ile Thr Gln Cys Phe Leu
1               5                   10

<210> SEQ ID NO 2
<211> LENGTH: 9
<212> TYPE: PRT
<213> ORGANISM: Homo sapiens

<400> SEQUENCE: 2

Ser Leu Leu Met Trp Ile Thr Gln Cys
1               5

<210> SEQ ID NO 3
<211> LENGTH: 9
<212> TYPE: PRT
<213> ORGANISM: Homo sapiens

<400> SEQUENCE: 3

Gln Leu Ser Leu Leu Met Trp Ile Thr
1               5

<210> SEQ ID NO 4
<211> LENGTH: 9
<212> TYPE: PRT
<213> ORGANISM: Homo sapiens

<400> SEQUENCE: 4

Tyr Met Asp Gly Thr Met Ser Gln Val
1               5

<210> SEQ ID NO 5
<211> LENGTH: 9
<212> TYPE: PRT
<213> ORGANISM: H. influenzae

<400> SEQUENCE: 5

Gly Ile Leu Gly Phe Val Phe Thr Leu
1               5

<210> SEQ ID NO 6
<211> LENGTH: 9
<212> TYPE: PRT
<213> ORGANISM: Artificial sequence
<220> FEATURE:
<221> NAME/KEY: Mutagen
```

```
<222> LOCATION: 9
<223> OTHER INFORMATION: Synthesized. Position 9 is mutated from Cys to
      Ala

<400> SEQUENCE: 6

Ser Leu Leu Met Trp Ile Thr Gln Ala
1               5

<210> SEQ ID NO 7
<211> LENGTH: 9
<212> TYPE: PRT
<213> ORGANISM: Artificial sequence
<220> FEATURE:
<221> NAME/KEY: Mutagen
<222> LOCATION: 9
<223> OTHER INFORMATION: Synthesized. Position 9 is mutated from Cys to
      Leu

<400> SEQUENCE: 7

Ser Leu Leu Met Trp Ile Thr Gln Leu
1               5

<210> SEQ ID NO 8
<211> LENGTH: 9
<212> TYPE: PRT
<213> ORGANISM: Artificial sequence
<220> FEATURE:
<221> NAME/KEY: Mutagen
<222> LOCATION: 9
<223> OTHER INFORMATION: Synthesized. Position 9 is mutated from Cys to
      Leu

<400> SEQUENCE: 8

Ser Leu Leu Met Trp Ile Thr Gln Val
1               5

<210> SEQ ID NO 9
<211> LENGTH: 34
<212> TYPE: DNA
<213> ORGANISM: Homo sapiens

<400> SEQUENCE: 9
gcaggatccc ggctcccatc ctcagggtga gggc                             34

<210> SEQ ID NO 10
<211> LENGTH: 9
<212> TYPE: PRT
<213> ORGANISM: Homo sapiens
<220> FEATURE:
<221> NAME/KEY: Mutagen
<222> LOCATION: 9
<223> OTHER INFORMATION: Syntheisized.  Xaa is any amino acid,
      preferably one with a non-polar side chain, such as Ala, Val, Leu,
      Ile, Pro, Phe, Met, Trp, or Gly

<400> SEQUENCE: 10

Ser Leu Leu Met Trp Ile Thr Gln Xaa
1               5

<210> SEQ ID NO 11
<211> LENGTH: 10
<212> TYPE: PRT
<213> ORGANISM: Homo sapiens

<400> SEQUENCE: 11

Ser Leu Leu Met Trp Ile Thr Gln Cys Phe
1               5                   10
```

```
<210> SEQ ID NO 12
<211> LENGTH: 9
<212> TYPE: PRT
<213> ORGANISM: Artificial sequence
<220> FEATURE:
<221> NAME/KEY: Mutagen
<222> LOCATION: 9
<223> OTHER INFORMATION: Synthesized. At position 9, of SEQ ID NO:2,Cys
      is replaced by Ile

<400> SEQUENCE: 12

Ser Leu Leu Met Trp Ile Thr Gln Ile
1               5

<210> SEQ ID NO 13
<211> LENGTH: 10
<212> TYPE: PRT
<213> ORGANISM: Artificial sequence
<220> FEATURE:
<221> NAME/KEY: Mutagen
<222> LOCATION: 10
<223> OTHER INFORMATION: Synthesized. At position 10, of SEQ ID NO: 11,
      Phe is replaced by Val

<400> SEQUENCE: 13

Ser Leu Leu Met Trp Ile Thr Gln Cys Val
1               5                   10

<210> SEQ ID NO 14
<211> LENGTH: 10
<212> TYPE: PRT
<213> ORGANISM: Artificial sequence
<220> FEATURE:
<221> NAME/KEY: Mutagen
<222> LOCATION: 10
<223> OTHER INFORMATION: Synthesized. At position 10 of SEQ ID NO: 11,
      Phe is replaced by Ile

<400> SEQUENCE: 14

Ser Leu Leu Met Trp Ile Thr Gln Cys Ile
1               5                   10

<210> SEQ ID NO 15
<211> LENGTH: 10
<212> TYPE: PRT
<213> ORGANISM: Artificial sequence
<220> FEATURE:
<221> NAME/KEY: Mutagen
<222> LOCATION: 9..10
<223> OTHER INFORMATION: Sythesized. At positions 9 and 10 of SEQ ID NO:
      11, Cys Phe is replaced by Ala Leu

<400> SEQUENCE: 15

Ser Leu Leu Met Trp Ile Thr Gln Ala Leu
1               5                   10

<210> SEQ ID NO 16
<211> LENGTH: 10
<212> TYPE: PRT
<213> ORGANISM: Artificial sequence
<220> FEATURE:
<221> NAME/KEY: Mutagen
<222> LOCATION: 9..10
<223> OTHER INFORMATION: Synthesized. At positions 9 and 10 of SEQ ID
      NO: 11, Cys Phe is replaced by Ala Ile

<400> SEQUENCE: 16

Ser Leu Leu Met Trp Ile Thr Gln Ala Ile
1               5                   10
```

```
<210> SEQ ID NO 17
<211> LENGTH: 10
<212> TYPE: PRT
<213> ORGANISM: Artificial sequence
<220> FEATURE:
<221> NAME/KEY: Mutagen
<222> LOCATION: 9
<223> OTHER INFORMATION: Synthesized. At position 9 of SEQ ID NO: 11,
      Cys is replaced by Ala

<400> SEQUENCE: 17

Ser Leu Leu Met Trp Ile Thr Gln Ala Phe
1               5                   10

<210> SEQ ID NO 18
<211> LENGTH: 10
<212> TYPE: PRT
<213> ORGANISM: Artificial sequence
<220> FEATURE:
<221> NAME/KEY: Mutagen
<222> LOCATION: 9..10
<223> OTHER INFORMATION: Synthesized.The first Xaa is Cys or Ala.  The
      second Xaa is any amino acid, and is preferablyVal, Phe, Ile or
      Leu

<400> SEQUENCE: 18

Ser Leu Leu Met Trp Ile Thr Gln Xaa Xaa
1               5                   10
```

NY-ESO-1 PEPTIDE DERIVATIVES, AND USES THEREOF

FIELD OF THE INVENTION

This invention relates to HLA binding peptides derived from an antigen associated with cancer. These peptides bind to Class I molecules, and provoke lysis of the cells to which they bind by cytolytic T lymphocytes.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369: 69 (1994) incorporated by reference, is based on acidic elution of peptides which have bound to MHC-class I molecules of tumor cells, followed by reversed-phase high performance liquid chromography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. No. 5,698,396, and patent application Ser. No. 08/479,328 filed Jan. 3, 1996. All three of these references are incorporated by reference. To summarize, the method involves the expression of cDNA libraries in a prokaryotic host. (The libraries are secured from a tumor sample). The expressed libraries are then immnoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has been applied to esophageal cancer samples, and an antigen has now been identified, and its encoding nucleic acid molecule isolated and cloned. See, e.g., U.S. Pat. No. 5,804,381, referred to supra. The antigen and truncated forms have been found to be reactive with antibodies in the serum of cancer patients. It has also been found that peptides derived form this molecule bind with MHC molecules, provoking both cytolytic T cell and helper T cell responses. It has been found that variations of these peptides can be used as well.

One difficulty in the area of cancer immunology is a lack of reliable protocols which can be used to identify and to quantify in vivo cytolytic T lymphocyte responses. As a result, it is difficult to characterize immune response, and to monitor vaccine trials. It has been found that analysis of cytolytic T cells is greatly facilitated by the use of complexes containing a plurality of T cell targets. More specifically, these complexes rely on the known avidity of two binding partners, such as avidin or streptavidin and biotin for each other. It is well known that every molecule of avidin/streptavidin can bind to four biotin molecules. Constructs where the avidin/streptavidin-biotin system is used to form complexes containing multiple targets for cytolytic T cells, i.e., a plurality of immune complexes which comprise an MHC molecule, such as an HLA molecule, a β2 microglobulin, and a peptide which binds to the HLA molecule are taught in, e.g. Ser. No. 09/049,850, filed Mar. 27, 1998, and incorporated by reference. The complex is labelled, and can be used to isolate, or to determine, cytolytic T cells of interest in a sample. Such complexes have been utilized in the invention which follows.

DETAILED DESCRIPTION OF PREFERRED EMBODIMENTS

EXAMPLE 1

Analysis of NY-ESO-1, as discussed in e.g., U.S. Pat. No. 5,804,381, showed that a presenting molecule for this antigen was HLA-A2. Hence, a screening of the amino acid sequence for NY-ESO-1 was carried out, to identify all peptides which satisfy this HLA-A2 binding motif, using the model set forth by D'Amaro et al., Human Immunol. 43: 13–18 (1995), and Drijfhout, et al., Human Immunol. 43: 1–12 (1995) incorporated by reference. Peptides corresponding to all of the amino acid sequences deduced thereby were synthesized, using standard techniques, and were then used in cytotoxicity assays, following Knuth et al., Proc. Natl. Acad. Sci. USA 81: 3511–3515 (1984), incorporated by reference. Specifically, cell line CEMX721.174.T2 ("T2" hereafter), was used, because it expresses HLA-A2, but does not process antigens to MHC complexed peptides, thereby making it ideal for experiments of the type described herein. Samples of T2 cells were labelled with 100 uCi of Na($^{51}$Cr) O$_4$, using standard methods, and were then washed three times, followed by incubation with 10 ug/ml peptide and 2.5 ug/ml of β2-microglobulin. Incubation was for one hour, at room temperature. Then responder cells (100 ul of a suspension of CTL NW38-IVS-1) were added, at an effector/target ratio of 90:1, and incubated for four hours in a water saturated atmosphere, with 5% CO$_2$, at 37° C. Then, plates were centrifuged at 200×g for five minutes, 100 ul of supernatant was removed, and radioactivity was measured. The percentage of $^{51}$Cr release was determined in accordance with known strategies. It was found that the peptides SLLMWITQCFL (SEQ ID NO: 1), SLLMWITQC (SEQ ID NO: 2), and QLSLLMWIT (SEQ ID NO: 3), were the three best stimulators of HLA-A2 restricted NY-ESO-1 specific CTLs. Comparable results were found when NW-MEL-38 and cell lines SK-MEL-37 and MZ-MEL-19 were used as targets.

EXAMPLE 2

In the next set of experiments, the ability of SEQ ID NOS: 1, 2 and 3 to bind to HLA-A2 molecules and to provoke CTL lysis was confirmed.

Samples of lymph nodes or metastatic lesions were taken from a patient who presented slowly progressive melanoma with recurrent metastases, all of which were localized to the same paravertebral region. Reverse transcriptase of RNA taken from a subject's tumor indicated that it expressed NY-ESO-1. Further, the patient's serum indicated high titer of anti-NY-ESO-1 antibodies.

The surgically resected lymph nodes or metastatic lesions were finely minced in sterile, RPMI 1640 medium that had been supplemented with 10% fetal calf serum. Suspensions of cells were placed in 24-well tissue culture plates, in 2 ml of Iscove's Dulbecco medium, supplemented with 0.24 mM Asn, 0.55 mM Arg, 1.5 mM Gln, 10% pooled human A+ serum, 100 U/ml IL-2, and 10 ng/ml of IL-7. The cells were cultured for 2–3 weeks, prior to being assayed via IFN-γ ELISPOT, in accordance with Czerkinsky, et al, J. Immunol. Meth 110:29 (1998), incorporated by reference. In brief, 2×10$^3$ cells/well of the short term culture referred to supra were combined with either 5×10$^4$ T2 cells/well, or the same number of T2 cells, plus 1 µM of one of SEQ ID NOS: 1–3. Each culture was run in duplicate.

A mean number of 19 spots were counted in the control cultures, 424 spots with SEQ ID NO: 2,358 spots with SEQ ID NO: 3, and 396 with SEQ ID NO: 1. These elevated numbers correspond to a frequency of about 1 NY-ESO-1 specific T cell per 20 tumor infiltrating lymphocytes. The reactive T cells were then cultured to monoclonality in accordance with Valmori, et al, J. Immunol 161: 6956 (1998), incorporated by reference. Five of 24 TIL derived clones derived for the TILs were found to be reactive with NY-ESO-1 derived peptides, when these were tested via CTL assays as described supra.

EXAMPLE 3

In these experiments, CTL ESO5, referred to supra, was tested for its ability to lyse A2$^+$ cells which either expressed or did not express NY-ESO-1. Cell lines NA8-MEL (A2$^+$, NY-ESO-1$^-$), SK-MEL37 (A2$^+$, NY-ESO-1$^+$), and Me 275 (A2$^+$, NY-ESO-1$^+$) were tested, in $^{51}$Cr release assays, as described supra.

The results indicated that NA8-Mel was lysed when NY-ESO-1 peptide SEQ ID NO: 2 was added, but not when it was absent. Presence or absence of SEQ ID NO: 2 was irrelevant to the lysis of SK-MEL 37 and Me 275, both of which were lysed under all conditions. These results indicate that CTL ESO 5 recognizes SEQ ID NO. 2 when exogenously added, and presented endogenously.

EXAMPLE 4

Experiments were then carried out to determine which of SEQ ID NOS: 1, 2 & 3 constituted the optimal T cell epitope for recognition by CTLs. To determine this, synthetic peptides corresponding to SEQ ID NOS: 1, 2 and 3 were tested in a functional competition binding assay, and then for recognition by specific CTLs.

The functional competition binding assay employed is that taught by Valmori, et al., J. Immunol 161:6956–6962 (1998), incorporated by reference, but elaborated upon herein.

The peptide YMDGTMSQV (SEQ ID NO: 4) is known to bind to HLA-A*0201 molecules, and to provoke lysis by an HLA-A*0201 restricted CTL clone, known as LAU 132/2. See Valmori, et al, Canc. Res. 59:2167 (1999). T2 cells were labelled with $^{51}$Cr, in the presence of anti class I monoclonal antibody W6/32. Varying concentrations of SEQ ID NO: 1, 2, or 3 (50 µl) were incubated with 50 µl samples of the labelled cells (1000 cells/well), for 15 minutes at room temperature. Then, a suboptimal dose (1 nM) of SEQ ID NO: 4 (50 µl) were added, together with 50 µl of the T cells (5000 cells/well). $^{51}$Cr release was measured after 4 hours incubation at 37° C. The concentration of each peptide required to achieve 50% inhibition of target cell lysis was then determined as [nM] 50%. In order to facilitate the comparison, relative competitive activity of each peptide was calculated as [nM] 50% of reference peptide FluMA 58-66 (SEQ ID NO: 5 GILGFVFTL), which is a known high affinity HLA-A*0201 binder, divided by the [nM] 50% value determined for the test peptides.

The results indicated that SEQ ID NO: 3 was a 100 fold less efficient competitor than SEQ ID NO: 4. Further, SEQ ID NO: 2 was 250 fold less efficient. Surprisingly, given their respective peptide lengths SEQ ID NO: 1 was 10 fold more competitive than SEQ ID NO: 2.

These results suggested that cysteine, as the carboxy terminal amino acid or SEQ ID NO: 2, was the cause of poor binding to HLA-A2 molecules. To investigate this, three derivatives of SEQ ID NO: 2 were prepared, replacing carboxy terminal cysteine with different hydrophobic amino acids containing non-polar side chains, such as alanine, leucine, or valine (SEQ ID NOS: 6–8, respectively). The functional competition assay described supra was carried out with each of these peptides. The results are presented in Table 1, which follows. All substitutions clearly and dramatically enhanced peptide binding, for all three substituted peptides, indicating that any hydrophobic residue at their position would have similar effects. ?

TABLE 1

| Peptide | Sequence | Relative competitor activity |
| --- | --- | --- |
| Influenza A matrix | | |
| 58-66 | GILGFVFTL (SEQ ID NO: 5) | 1 |
| NY-ESO-1: | | |
| 155-163 | QLSLLMWIT (SEQ ID NO: 3) | 0.01 |
| 157-167 | SLLMWITQCFL (SEQ ID NO: 1) | 0.04 |
| 157-165 | SLLMWITQC (SEQ ID NO: 2) | 0.004 |
| 157-C165A | SLLMWITQA (SEQ ID NO: 6) | 0.4 |
| 157-C165L | SLLMWITQL (SEQ ID NO: 7) | 0.5 |
| 157-C165V | SLLMWITQV (SEQ ID NO: 8) | 10 |

EXAMPLE 5

As indicated, supra, the peptides described herein were tested for recognition by specific CTLs. In these experiments, target T2 cells were labelled with $^{51}Cr$ for 1 hour, at 37° C., and then washed two times. Sample (1000 labelled cells in 50 μl) were then incubated with varying concentrations of peptide, for 15 minutes. Effector cells (50 μl) were then added. These effector cells are ESO1 specific CTL clone ESO5. The lymphocyte: target ratio was 30:1. Chromium release was measured after 4 hours of incubation at 37° C., by testing 100 μl supernatant samples.

Specific percent lysis was calculated as:

$$100 \times \frac{[(\text{experimental} - \text{spontaneous release})]}{(\text{total} - \text{spontaneous release})}$$

The results, which follow in Table 2, are presented as the peptide nanomolar concentration giving 50% maximal activity. Also presented in Table 2 is the "relative antigenic activity" value, which is calculated as [nM] 50% of the peptide SEQ ID NO: 2 divided by [nM] 50% of the test peptide. Recognition of the analogue peptides by CTL was comparable to, or better than, the parental peptide. These results demonstrate that, among natural NY-ESO-1 peptides, SEQ ID NO: 2 was the optimally recognized antigenic peptide. Further, of the substituted peptides, SEQ ID NO: 8 was recognized as efficiently as SEQ ID NO: 2, and the others were recognized more efficiently. SEQ ID NO: 6 was 1000 fold more efficiently recognized than SEQ ID NO: 2.

TABLE 2

| Peptide Sequence | Peptide ([nM] 50%) | Relative antigenic activity |
| --- | --- | --- |
| SLLMWITQC | 0.6 | 1 |
| SLLMWITQA | 0.0005 | 1,200 |
| SLLMWITQL | 0.01 | 60 |
| SLLMWITQV | 1 | 0.6 |
| QLSLLMWIT | 50 | 0.012 |
| SLLMWITQCFL | 50 | 0.012 |

EXAMPLE 6

This experiment describes the basic technique for making tetrameric complexes of antigen, used in the examples which follow. In order to make the desired tetramers, it was first necessary to prepare constructs which would encode modified HLA-A*0201 molecules. To do this, total RNA was extracted from HLA-A*0201 positive cells, and HLA-A*0201 was then cloned, using specific primers for the molecule, and reverse transcription polymerase chain reaction (RT-PCR). Altman et al., Science 274: 94–96 (Oct. 4, 1996) but with a new 3' primer, i.e. 5'-GCAGGATCCCGGCTCCCATCCTCA GGGTGAGGGGC-3' (SEQ ID NO: 9) incorporated by reference, was followed. Simultaneously with the RT-PCR, the amino terminal nucleotide sequence was altered to optimize protein expression in the vector used. See Garboczi et al., Proc. Natl. Acad. Sci. USA 89: 3429 (1992) incorporated by reference. Once this was done, the extracellular coding portion of the molecule was amplified, again using specific primers. The resulting construct was recloned into a vector which would produce a BirA biotinylation recognition site in frame at the 3'-end of the HLA-A*0201 heavy chain. The modified HLA-A*0201 and β2 microglobulin were overexpressed in separate E. coli cultures. The resulting inclusion bodies were purified and the HLA and β2 microglobulin recombinant proteins were solubilized into urea, and then refolded, in a refolding solution, at 4° C. to form complexes. (The refolding solution contained 100 mM Tris, at pH 8.0, L-arginine, 400 mM, EDTA, 2 mM, reduced glutathione, 5 mM, oxidized glutathione, 0.5 mM, PMSF, 0.1 mM, HLA heavy chain, and β2 microglobulin 1 μM, and 10 μM of the peptide of interest). The refolding solution was concentrated to 7.5 ml, using standard techniques. Then, refolding buffer was exchanged with BirA reaction buffer (Tris 100 mM, pH 7.5, NaCl 200 mM, Mg Cl$_2$ 5 mM, PMSF 100 μM, leupeptin 1 μM, and pepstatin 1 μM), the last three being added immediately before use.

The complexes were then biotinylated with biotin holoenzyme synthase (the BirA enzyme) by combining the refold mix containing the HLA-A2 complex with 50 μM enzyme, 100 mM biotin in 200 mM Tris, and 100 mM adenosine triphosphate. The mixture was incubated overnight at room temperature. The biotinylated complexes were then purified, and combined with phycoerythrin-labelled streptavidin, to produce tetrameric structures. These were isolated, and reconstituted in small volumes, at a concentration of 1 mg/ml.

EXAMPLE 7

These experiments were designed to assess the frequency of NY-ESO-1 specific T cells. Fluorescent tetramers of biotin, HLA-A2, and peptides were prepared in accordance with Romero, et al, J. Exp. Med. 188:641 (1998), and Altman, et al, Science 274:94 (1996), Example 6, supra, as well as patent application Ser. No. 09/275,993 filed Mar. 25, 1999 and Ser. No. 09/049,850, filed Mar. 27,1998, both of which are incorporated by reference. As antigenic peptides, Flu Ma 58-66 (SEQ ID NO: 5), and the ESO-1 derivative using alanine as carboxy terminus (SEQ ID NO: 6) were used. This derivative was selected because of its high affinity, since high affinity binding to HLA-A2 facilitates generation of stable tetramers.

Following tetramer assembly, CTL clones specific for the peptides were combined with the appropriate tetramers in 20 μl of PBS with 2% FCS, and incubated at room temperature for 1 hour, followed by addition of either 20 μl of anti-CD8 antibodies labeled with FITC, or a mixture of anti-CD8 antibodies labeled with FITC, and anti-CD45RA antibodies labeled with "CYC." This mixture was incubated for 30 minutes at 4° C., after which the cells were washed in the same buffer as described supra, and then analyzed by flow cytometry.

The tetramers of the NY-ESO-1 derivative (SEQ ID NO: 6) specifically stained ESO 5, but did not stain the T cells specific for FluMa, and vice versa.

EXAMPLE 8

These experiments were designed to validate the use of tetramers which contain NY-ESO-1 peptides in detecting and isolating NY-ESO-1 specific T cells.

An enriched CD8$^+$ T cell sample which had been stimulated with either SEQ ID NO: 2, or the alanine terminal substitution (SEQ ID NO: 6). (Stimulation was accomplished by loading autologaus antigens presenting cells with the peptide of interest).

Tetramers were made, as described supra, and used to stain the CD8$^+$ cells fourteen days following stimulation. Cells were sorted, and tested by IFN-γ ELISPOT, as described supra.

Only CD8$^+$ tetramer$^+$ cells were found to contain IFN-γ productive cells.

Sorted CD8$^+$ tetramer$^+$ and CD8$^+$ tetramer$^-$ cells were expanded for two weeks via PHA stimulation, and both populations were assayed, in a $^{51}$Cr release assay, on Me 275 and T2 cells, described supra, which had or had not been pulsed with SEQ ID NO: 2.

Only CD8$^+$ tetramer$^+$ cells were effective in killing both cells which had been pulsed with SEQ ID NO: 2 and cells pulsed with the alanine analog.

EXAMPLE 9

These experiments were designed to determine if NY-ESO-1 antigen is processed intracellularly to produce a peptide that is presented by HLA-A2 molecules, which in turn stimulates lysis by CTLs.

Tetramers, as described in example 6, supra, were prepared, using the peptide of SEQ ID NO: 2. These tetramers were then used to stain a sample of cells taken from a patient who had been diagnosed previously as having a NY-ESO-1 positive melanoma. See Dunbar, et al., J. Immunol 162(12):6959–62(1999) and Ser. No. 09/049,850, filed Mar. 27, 1998, incorporated by reference. In brief, however, peripheral blood lymphocyte ("PBL") samples were stained with tetramers for 15 minutes at 37° C., followed by washing in PBS/1% FCS at 37° C., followed by incubation with a labelled, anti-CD8 antibody for 30 minutes, on ice. The cells were then washed three times, in ice cold PBS/1% FCS, and were then analyzed via flow cytometry. Positive cells: were cloned, via pulsing the positive cells with 10 μM of the peptide of SEQ ID NO: 2, and culturing in 1 L-2 (200 u/ml) for 5 days.

Four of these positive CTLs were expanded, and tested in the experiments which follow.

EXAMPLE 10

The CTLs described supra were then tested for killing specificity. To do so, samples of a cell line typed previously as being NY-ESO-1 positive, a cell line typed previously as being NY-ESO-1 negative, samples of T2 cells which had been pulsed with 1 μM of the peptide of SEQ ID NO: 2, and samples of unpulsed T2 cells were combined with the CTLs, in 1:1 and 0.3:1 effector/target ratios. Killing was determined using the $^{51}$Cr release assay described supra.

The results indicated that both the NY-ESO-1 positive cells, and the T2 cells pulsed with SEQ ID NO: 2 were killed, while the others were not, demonstrating that intracellular processing of NY-ESO-1 results in the generation of a peptide which is recognized by SEQ ID NO: 2 specific CTLs.

EXAMPLE 11

The experiments in this example were designed to determine whether a mixture of different CTLs was responsible for the positive results obtained with SEQ ID NOS: 1, 2 and 3, or if a single CTL clone recognized all peptides. In these experiments, T2 cells were pulsed with one of SEQ ID NO: 2, SEQ ID NO: 1, or a peptide consisting of NY-ESO-1 amino acids 157–166, i.e.:

SLLMWITQCF (SEQ ID NO: 11).

SEQ ID NO: 3 was also tested, as was a peptide consisting of the first 8 amino acids of SEQ ID NO: 1. Varying concentrations of peptide were used to pulse T2 cells. As a control, SEQ ID NO: 5 was used. The same $^{51}$Cr release assay described supra was used. Prior to testing the CTLs, these were assayed to determine if they each expressed a single T cell receptor.

The results indicated that all T cells recognized SEQ ID NOS:2, 3 and 11, but failed to recognize SEQ ID NO: 1 or the truncated peptide 157–164, i.e., a peptide consisting of the first 8 amino acids of SEQ ID NO: 11. These indicate that all three peptides were recognized by clonal CTLs.

EXAMPLE 12

The experiments set forth in this example were designed to determine the intracellular processing requirements for generating the peptide of SEQ ID NO: 2.

Cerundolo, et al. Nature 345(6274):449–52(1990) have described mutant processing cells which are characterized as having defined blocks in the MHC I processing pathways. These cells were used in these experiments. Specifically, a parental cell line was used, i.e., "line 45," as well as "line. 174," which was TAP, LMP2, and LMP7 negative, a transfectant of line. 174, where the line was transfected with vectors encoding TAP1 and TAP2, and a transfectant of line. 174 which had been transfected with vectors encoding TAP1, TAP2, and LMP7. (The abbreviation "TAP" refers to "transporter associated with antigen processing," and the abbreviation "LMP" refers to "low molecular mass polyprotein.")

In addition to the transfectants described supra, all of the cells were transfected with vaccinia virus constructs which encoded NY-ESO-1, at a multiplicity of infection (M.O.I.) of 5, for 90 minutes.

As controls, equivalent numbers of cells ($10^6$ cells) were suspended in 50 µl of medium containing 100 µM of lactacysetine, for 1 hour prior to addition of vaccinia virus constructs. After the 90 minute infection period, cells were washed, and suspended in 5 ml of medium containing 1 µM of lactacystin, and grown overnight to allow expression of the vaccinia vector. LMP2 and LMP7 are proteosome subunits.

The cells were then combined with CTLs in a $^{51}$Cr release assay of the type described supra.

The results indicated that the expression of vaccinia encoded NY-ESO-1 in TAP deficient cells failed to sensitize them for CTL lysis. On the other hand, the presence or absence of the proteosome subunits LMP2 and LMP7 did not impair the presentation of an epitope recognized by the CTLs. The controls used support this, because .174/TAP cells did not present the peptide of SEQ ID NO: 5, which is known to be dependent on LMP7 for presentation, while transfection with a vector encoding LMP7, or the addition of lactacysteine eliminated the block on presentation.

These results suggest, quite strongly, that a non-proteosomal protease is involved in the presentation of the NY-ESO-1 epitope.

EXAMPLE 13

These experiments were designed to determine if peptide analogues of SEQ ID NO: 2, prepared by modification of the C-terminal cysteine residue, had changed immunogenicity. $^{51}$Cr release assays of the type supra were carried out, in which the peptide (SEQ ID NO: 2), and target cells were combined with 200 µM of either dithiothreital (DTT) or TCEP (Tris 2 carboxymethyl phosphine).

The results indicate that, in the presence of reducing agent, antigenicity of SEQ ID NO: 2 increased 10 fold. Parallel experiments were carried out with SEQ ID NO: 8, and there was no increase in antigenicity.

EXAMPLE 14

The results observed in example 13, supra, suggested testing modified peptides. In addition to the peptides of SEQ ID NOS:7 and 8, a peptide of formula:

SLLMWITQI (SEQ ID NO: 12), was synthesized, as were the following 10 mers:

SLLMWITQCV (SEQ ID NO: 13)
SLLMWITQCF (SEQ ID NO: 11, described supra)
SLLMWITQCI (SEQ ID NO: 14)
SLLMWITQAL (SEQ ID NO: 15)
SLLMWITQAI (SEQ ID NO: 16)
SLLMWITQAF (SEQ ID NO: 17)

Further, SEQ ID NO: 2 was prepared where the C-terminal cysteine was modified with an —$NH_2$—CO—$CH_2$ sidechain. All of these peptides were tested in CTL assays of the type described supra. The peptides of SEQ ID NOS:7, 8 and 12 all increase recognition by NY-ESO-1 157–165 specific CTLs by about 1000 fold, as compared to SEQ ID NO: 2. The peptide of SEQ ID NO: 14 was also recognized more efficiently than SEQ ID NO: 2.

EXAMPLE 15

In these experiments, the ability of different peptide analogues to stimulate proliferation of NY-ESO-1 specific CTLs was tested.

In brief, PBLs were taken from two melanoma patients who evidenced high titers of NY-ESO-1 specific antibodies, using a standard assay. These PBLs were then stimulated with either 100 nM or 10 nM, of either SEQ ID NO: 2 or SEQ ID NO: 8 following standard protocols. Over a period of two weeks, SEQ ID NO: 8 resulted in a 14 fold greater expansion of NY-ESO-1 specific CTLs. Over a 3 week period, the expansion was 54 fold greater than that obtained using SEQ ID NO: 2. These CTLs were stained with tetramers of the type described supra, using SEQ ID NO: 2, and the staining was positive, indicating that the CTLs recognized the relevant NY-ESO-1 epitope.

It is noteworthy that 10 nM of SEQ ID NO: 8 stimulated the CTLs, while larger amounts of native peptide were in fact necessary. Further, in follow up experiments using standard methodologies, it was ascertained that the expanded CTLs described in this example were capable of killing NY-ESO-1 positive tumor cells.

The invention, as will be seen from the preceding disclosure, relates to peptides, of sequence:

SLLMWITQX (SEQ ID NO: 10)

wherein X is any amino acid except cysteine, is preferably a hydrophobic amino acid with a non-polar side chain, such as Ala, Val, Leu, Ile, Pro, Phe, Met, Trp or Gly and is most preferably Ala, Ile, Val or Leu. These peptides may be used therapeutically, via administration to a patient who is HLA-A2 positive, and expresses NY-ESO-1 in connection with a pathology, as well as diagnostically, i.e., to determine if HLA-A2 positive cells are present, or if relevant CTLs are present, and so forth.

In an alternate embodiment, X is two amino acids, the first of which is cysteine or alanine, and the second of which is any amino acid. Preferably, the second amino acid is Phe, Ile, Val or Leu. Most preferably in this embodiment, the first amino acid is cysteine, and the second amino acid is Phe or Ile, as in SEQ ID NO: 11, or 14.

The HLA-A2 molecule is an MHC Class I molecule, and T cells which respond to complexes of peptides and class I molecules are generally CD8+ cells.

Exemplary of the peptides defined by the core sequence of SEQ ID NO: ID NO. 10 is the peptide defined by SEQ ID NO: ID NO: 6. This peptide, as indicated, binds to HLA-A2 molecules. Hence it is a "marker" for HLA-A2, as well as a component of peptide/MHC complexes which stimulate proliferation of CTLs, as is described supra. Similarly, peptides where Ile, Leu or Val is the carboxy terminus in the structure of SEQ ID NO: 10 can be used.

The peptides may be combined with adjuvants to form therapeutic compositions. Also a part of the invention are nucleic acid molecules which consist of nucleotide sequences (so-called "mini-genes") which encode the peptides of the invention. These mini-genes can be incorporated into expression vectors, in operable linkage with a promoter. Additional constructs which encode more than one peptide of the invention, including multiple copies of one or more peptides, are part of the invention. These constructs may be, e.g. in the form of recombinant vectors, or so-called "naked DNA", i.e. small nucleic acid molecules encoding the desired peptide or peptides. Similarly, recombinant cells which include the DNA or the vectors, such as eukaryotic or prokaryotic cells, are part of the invention.

The ability of these peptides to bind to HLA molecules makes them useful as agents for determining presence of HLA-A2 positive cells, such as HLA-A*0201 positive cells, by determining whether or not the peptides bind to cells in a sample. This "ligand/receptor" type of reaction is well known in the art, and various methodologies are available for determining it.

A further aspect of the invention are so-called "mini genes" which carry information necessary to direct synthesis of peptides via cells into which the mini genes are, transfected. Mini genes can be designed which encode one or more antigenic peptides, and are then transferred to host cell genomes via transfection with plasmids, or via cloning into vaccinia or adenoviruses. See, e.g., Zajac, et al., *Int. J. Cancer* 71: 496 (1997), incorporated by reference These recombinant vectors, such as recombinant vaccinia virus vectors, can be constructed so as to produce fusion proteins. For example, as was shown, supra, fusion proteins can be constructed where one portion of the fusion protein is the desired tumor rejection antigen precursor, or tumor rejection antigen, and additional protein or peptide segments can be included. Exemplary, but by no means the only types of additional protein or peptide segments which can be added to the fusion proteins, are reporter proteins or peptides, i.e., proteins or peptides which give an observable signal so as to indicate that expression has occurred, such as green fluoresence protein. Additional reporter proteins include, but are by no means limited to, proteins such as βgalactosidase, luciferase, dhfr, and "eGFP", or enhanced green fluorescent protein, as described by Cheng, et al., Nature Biotechnology 14:606 (1996), incorporated by reference, and so forth. The various reporter proteins available to the skilled artisan can be, and are used, in different ways. For example, "GFP" and "eGFP" can be used to visualize infected cells, thereby facilitating tracking when flow cytometry is used, and the isolation of the cells so infected. Other reporter proteins are useful when methods such as western blotting, immunoprecipitation, and so forth are used. These techniques are standard in the art and need not be reiterated here. Protein or peptide segments which facilitate the cleavage of the tumor rejection antigen precursor or tumor rejection antigen from the fusion peptide may also be included. The fusion protein can include more than one tumor rejection antigen, as described, supra, and can also include proteins or peptides which facilitate the delivery of the tumor rejection antigen or antigens to a relevant MHC molecule. Such proteins and peptides are well known to the art, and need not be elaborated herein.

Also a part of the invention are recombinant cells which have been transfected with the recombinant reporter vectors described herein. Such cells may be, e.g., any type of eukaryotic cell, with human cells being especially preferred. Such cells can then be used, e.g., to produce tumor rejection antigen precursors or tumor rejection antigens. They can also be used, in an ex vivo context, to generate cytolytic T cells specific for particular complexes of MHC molecules and tumor rejection antigens. This can be done simply by contacting the transfected cells to a source of T cells, such as a blood sample, so as to provoke the proliferation of any cells in the sample specific to the complexes of MHC molecules and TRAs (i.e., tumor rejection antigens) produced following expression of the fusion protein, and processing of the TRA. Such cells, when rendered nonproliferative, can also be used as vaccine materials, as they will present the relevant complexes on their surface, and provoke the same type of T cell response in vivo, as is shown herein. Similarly, the vectors can be used as vaccine materials per se, and can be administered to a patient in need of a T cell response against complexes of MHC molecules and peptide on cell surfaces. Of course, T cells generated ex vivo can also be used to treat patients.

The peptides may be combined with peptides that are other tumor rejection antigens to form "polytopes." Exemplary peptides include those listed in U.S. patent application Ser. No. 08/672,351 filed Jun. 25, 1996, now abandoned, Ser. No. 08/718,964, now U.S. Pat. No. 5,932,694, Ser. No. 08/487,135 now U.S. Pat. No. 5,821,122, Ser. No. 08/530, 569, now U.S. Pat. No. 5,939,526, and Ser. No. 08/880,963, now U.S. Pat. No. 6,025,470, all of which are incorporated by reference.

Additional peptides which can be used are those described in the following references, all of which are incorporated by reference: U.S. Pat. Nos. 5,405,940; 5,487,974; 5,519,117; 5,530,096; 5,554,506; 5,554,724; 5,558,995; 5,585,461; 5,589,334; 5,648,226; and 5,683,886; PCT International Publication Nos. 92/20356; 94/14459; 96/10577; 96/21673; 97/10837; 97/26535; and 97/31017 as well as pending U.S. application Ser. No. 08/713,354, filed Sep. 13, 1996, now U.S. Pat. No. 6,265,215.

Polytopes are groups of two or more potentially immunogenic or immune stimulating peptides, which can be joined together in various ways, to determine if this type of molecule will stimulate and/or provoke an immune response.

These peptides can be joined together directly, or via the use of flanking sequences. See Thompson et al., *Proc. Natl. Acad. Sci. USA* 92(13): 5845–5849 (1995), teaching the direct linkage of relevant epitopic sequences. The use of polytopes as vaccines is well known. See, e.g., Gilbert et al., *Nat. Biotechnol.* 15(12): 1280–1284 (1997); Thomson et al., supra; Thomson et al., *J. Immunol.* 157(2): 822–826 (1996); Tam et al., *J. Exp. Med.* 171(1): 299–306 (1990), all of which are incorporated by reference. The Tam reference in particular shows that polytopes, when used in a mouse model, are useful in generating both antibody and protective immunity. Further, the reference shows that the polytopes, when digested, yield peptides which can be and are presented by MHCs. Tam shows this by showing recognition of individual epitopes processed from polytope 'strings' via CTLs. This approach can be used, e.g., in determining how many epitopes can be joined in a polytope and still provoke recognition and also to determine the efficacy of different combinations of epitopes. Different combinations may be 'tailor-made' for the patients expressing particular subsets of tumor rejection antigens. These polytopes can be introduced as polypeptide structures, or via the use of nucleic acid delivery systems. To elaborate, the art has many different ways available to introduce DNA encoding an individual epitope, or a polytope such as is discussed supra. See, e.g., Allsopp et al., *Eur. J. Immunol.* 26(8); 1951–1959 (1996), incorporated by reference. Adenovirus, pox-virus, Ty-virus like particles, plasmids, bacteria, etc., can be used. One can test these systems in mouse models to determine which system seems most appropriate for a given, parallel situation in humans. They can also be tested in human clinical trials.

Also, a feature of the invention is the use of these peptides to determine the presence of cytolytic T cells in a sample. It was shown, supra, that CTLs in a sample will react with peptide/MHC complexes. Hence, if one knows that CTLs are in a sample, HLA A2 positive cells can be "lysed" by adding the peptides of the invention to HLA-A2 positive cells, such as HLA-A*0201 positive cells, and then determining, e.g., radioactive chromium release, TNF production, etc. or any other of the methods by which T cell activity is determined. Similarly, one can determine whether or not specific tumor infiltrating lymphocytes ("TILs") are present in a sample, by adding one of the claimed peptides with HLA-A2 positive cells to a sample, and determining lysis of the HLA-A2 positive cells via, e.g., $^{51}$Cr release, TNF presence and so forth. In addition, CTL may be detected by ELISPOT analysis. See for example Schmittel et al., (1997). *J. Immunol. Methods* 210: 167–174 and Lalvani et al., (1997). *J. Exp. Med.* 126: 859 or by FACS analysis of fluorogenic tetramer complexes of MHC Class I/peptide (Dunbar et al., (1998), *Current Biology* 8: 413–416, Romero, et al., *J. Exp. Med.* 188: 1641–1650 (1998). All are incorporated by reference. To elaborate, the complexes comprise a first binding partner and a second binding partner, wherein the first and second binding partner are specific for each other. These can be, e.g., avidin or streptavidin and biotin, an antibody or a binding portion of an antibody specific to biotin, and so forth. The key feature is that the second binding partner must be bound to a plurality of complexes of an MHC molecule, a β2 microglobulin molecule and a peptide which binds specifically to said MHC molecule, and the multicomponent complex must be labelled. The MHC molecules are preferably HLA-A2 molecules; however, it will be understood by the artisan of ordinary skill that any HLA molecule could be used.

Preferably, the second binding partner is biotin, but it may also be, e.g., an antibody which is specific for a component of the HLA/β2 microglobulin/peptide complex, such as an HLA specific antibody, or a β2 microglobulin specific antibody. Similarly, the first binding partner may be e.g., recombinant or naturally occurring protein L, recombinant or naturally occurring protein A, or even a second antibody. The complex can be in soluble form, or bound, e.g., to a removable solid phase, such as a magnetic bead.

The number of HLA/β2 microglobulin/peptide complexes in the large molecule of the invention may vary. It comprises at least two complexes, and preferably at least four, but more may be present as well.

The complex of binding partners and HLA/β2 microglobulin/peptide may be labelled, using any of the labels known to the art. Examples of fluorescent labels are given supra. Enzymatic labels, such as alkaline phosphatase, metal particles, colored plastics made of synthetic materials, radioactive labels, etc., may all be used.

A third binding partner may also be used, which binds, specifically, to the first binding partner. For example, if the first binding partner is streptavidin, and the second binding partner is biotin, then the third binding partner may be a streptavidin specific antibody. When three or more binding partners are used, the label referred to supra may be attached to any of the binding partners so long as engagement with the HLA/β2 microglobulin peptide complexes is not impaired.

The complexes may be used, e.g., to identify or to isolate cytolytic T cells present in a sample, where these cells are specific for the HLA/β2 microglobulin/peptide complex. Such cytolytic T cells bind to the immunocomplexes of the invention. In a preferred embodiment, the sample being tested is treated with a reactant which specifically binds to a cytolytic T cell, wherein said label provides a detectable signal. The sample, including labelled CTLs, is then contacted to the complex, where it binds, and can be separated via any of the standard, well known approaches to cell separation. Preferably, FACS is used, but other separation methodologies will be known to the skilled artisan as well. The peptide used is left to the needs of the skilled artisan, and will depend, e.g., on the nature of the specific MHC system under consideration.

Additionally, the method can be used to monitor the status of tumors, following administration of a particular therapeutic agent, such as a vaccine. Further, since the methodology can be used to identify cytolytic T cell precursors, as shown, supra, one can identify candidates for potential therapies by determining if they possess the relevant T cell precursors.

Of course, the peptides may also be used to provoke production of CTLs. As was shown, supra, CTL precursors develop into CTLs when confronted with appropriate complexes. By causing such a "confrontation" as it were, one may generate CTLs. This is useful in an in vivo context, as well as ex vivo, for generating such CTLs.

Also a part of the invention are so-called "cocktails" comprising a plurality of different peptides, at least one of which is a peptide of the invention, as well as "polytope" molecules, and nucleic acid molecules encoding them. "Polytope" as used herein, refers to a recombinant molecule designed to contain a plurality of peptide sequences which are presented by MHC molecules, following intracellular processing. Such polytopes can consist of a repeating epitope, a number of different epitopes, and so forth.

Other features and applications of the invention will be clear to the skilled artisan, and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

I claim:

1. An isolated decapeptide of formula:

SLLMWITQXX (SEQ ID NO: 18) wherein the first X is cysteine, and the second X is Ile, Val, or Leu.

2. An isolated decapeptide of formula:

SLLMWITQXX (SEQ ID NO: 18) wherein the first X is alanine, and the second X is any amino acid.

3. The isolated decapeptide of claim 2, wherein the second X is Phe, Ile, Val or Leu.

4. The isolated decapeptide of claim 1, wherein the second X is Ile (SEQ ID NO: 14).

5. The isolated decapeptide of claim 1, wherein the second X is Val (SEQ ID NO: 13).

6. The isolated decapeptide of claim 1, wherein the second X is Leu (SEQ ID NO: 18).

7. The isolated decapeptide of claim 3, wherein the second X is Phe (SEQ ID NO: 17).

8. The isolated decapeptide of claim 3, wherein the second X is Ile SEQ ID NO: 16).

9. The isolated decapeptide of claim 3, wherein the second X is Val (SEQ ID NO: 18).

10. The isolated decapeptide of claim 3, wherein the second X is Leu (SEQ ID NO: 15).

11. A composition useful in provoking a cytolytic T cell response comprising the isolated decapeptide of claim 1, and an adjuvant.

12. A composition useful in provoking a cytolytic T cell response comprising the isolated decapeptide of claim 2, and an adjuvant.

13. The composition of claim 1, further comprising at least one additional tumor rejection antigen.

14. The composition of claim 2, further comprising at least one additional tumor rejection antigen.

* * * * *